United States Patent
Alvarez

(10) Patent No.: US 9,504,604 B2
(45) Date of Patent: Nov. 29, 2016

(54) LITHOTRIPSY EYE TREATMENT

(71) Applicant: Auris Surgical Robotics, Inc., San Carlos, CA (US)

(72) Inventor: Jeffery B. Alvarez, San Carlos, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 380 days.

(21) Appl. No.: 13/711,440

(22) Filed: Dec. 11, 2012

(65) Prior Publication Data

US 2014/0012276 A1   Jan. 9, 2014

Related U.S. Application Data

(60) Provisional application No. 61/576,629, filed on Dec. 16, 2011.

(51) Int. Cl.
| | |
|---|---|
| *A61F 9/00* | (2006.01) |
| *A61F 9/007* | (2006.01) |
| *A61B 17/22* | (2006.01) |
| *A61B 17/24* | (2006.01) |
| *A61B 17/00* | (2006.01) |

(52) U.S. Cl.
CPC ....... *A61F 9/00736* (2013.01); *A61B 17/2202* (2013.01); *A61B 17/22022* (2013.01); *A61F 9/00745* (2013.01); *A61B 17/24* (2013.01); *A61B 2017/00331* (2013.01); *A61B 2017/22021* (2013.01); *A61B 2017/22024* (2013.01); *A61B 2017/22025* (2013.01); *A61B 2017/22062* (2013.01)

(58) Field of Classification Search
CPC .............. A61B 17/2202; A61B 17/22022; A61B 17/24; A61B 2017/00331; A61B 2017/22024; A61B 2017/22025; A61B 2017/22062
USPC ................ 606/32, 33, 37, 39, 41, 45, 166
See application file for complete search history.

(56) References Cited

U.S. PATENT DOCUMENTS

| | | | |
|---|---|---|---|
| 4,597,388 | A | 7/1986 | Koziol et al. |
| 4,905,673 | A | 3/1990 | Pimiskern |
| 5,425,735 | A | 6/1995 | Rosen et al. |
| 5,472,406 | A | 12/1995 | De La Torre et al. |
| 5,572,999 | A | 11/1996 | Funda et al. |

(Continued)

FOREIGN PATENT DOCUMENTS

| | | |
|---|---|---|
| JP | H09224951 A | 9/1997 |
| WO | WO 92/14411 A1 | 9/1992 |

(Continued)

OTHER PUBLICATIONS

International search report and written opinion dated Mar. 29, 2013 for PCT/US2012/069540.

(Continued)

*Primary Examiner* — Ashley Fishback
(74) *Attorney, Agent, or Firm* — Wilson, Sonsini, Goodrich & Rosati

(57) ABSTRACT

A lithotripsy probe is used to break up cataracts, sinus blockages and other body masses, where the broken materials may be removed by suction. The lithotripsy probe may have a spark generator, a fluid motion generator, or other component for breaking up the body mass.

14 Claims, 6 Drawing Sheets

(56) References Cited

U.S. PATENT DOCUMENTS

| | | |
|---|---|---|
| 5,662,590 A | 9/1997 | De La Torre et al. |
| 5,695,461 A * | 12/1997 | Schaible ............... A61F 9/008 604/22 |
| 5,695,500 A | 12/1997 | Taylor et al. |
| 6,033,371 A | 3/2000 | Torre et al. |
| 6,326,616 B1 * | 12/2001 | Andrien et al. ............. 250/288 |
| 6,398,792 B1 | 6/2002 | O'Connor |
| 6,406,486 B1 | 6/2002 | De La Torre et al. |
| 6,436,107 B1 | 8/2002 | Wang et al. |
| 6,554,793 B1 | 4/2003 | Pauker et al. |
| 6,638,246 B1 | 10/2003 | Naimark et al. |
| 6,671,581 B2 | 12/2003 | Niemeyer et al. |
| 6,736,784 B1 | 5/2004 | Menne et al. |
| 6,763,259 B1 | 7/2004 | Hauger et al. |
| 7,087,061 B2 | 8/2006 | Chernenko et al. |
| 7,344,528 B1 | 3/2008 | Tu et al. |
| 7,351,193 B2 * | 4/2008 | Forman et al. .................. 600/3 |
| 7,725,214 B2 | 5/2010 | Diolaiti |
| 7,883,475 B2 | 2/2011 | Dupont et al. |
| 7,967,799 B2 | 6/2011 | Boukhny |
| 8,049,873 B2 | 11/2011 | Hauger et al. |
| 8,224,484 B2 | 7/2012 | Swarup et al. |
| 8,414,564 B2 | 4/2013 | Goldshleger et al. |
| 8,518,024 B2 | 8/2013 | Williams et al. |
| 2004/0030349 A1 | 2/2004 | Boukhny |
| 2005/0070844 A1 | 3/2005 | Chow et al. |
| 2006/0229598 A1 * | 10/2006 | Shadduck ............. A61B 18/148 606/41 |
| 2007/0032906 A1 | 2/2007 | Sutherland et al. |
| 2007/0135733 A1 | 6/2007 | Soukup et al. |
| 2007/0135763 A1 | 6/2007 | Musbach et al. |
| 2007/0299427 A1 | 12/2007 | Yeung et al. |
| 2008/0065109 A1 | 3/2008 | Larkin |
| 2008/0097293 A1 | 4/2008 | Chin et al. |
| 2008/0114341 A1 | 5/2008 | Thyzel |
| 2008/0177285 A1 | 7/2008 | Brock et al. |
| 2008/0187101 A1 | 8/2008 | Gertner |
| 2008/0228104 A1 | 9/2008 | Uber et al. |
| 2009/0171271 A1 | 7/2009 | Webster et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0312768 A1 | 12/2009 | Hawkins et al. |
| 2009/0326322 A1 | 12/2009 | Diolaiti |
| 2010/0036294 A1 | 2/2010 | Mantell et al. |
| 2010/0073150 A1 | 3/2010 | Olson et al. |
| 2011/0009779 A1 | 1/2011 | Romano et al. |
| 2011/0028887 A1 * | 2/2011 | Fischer ............. A61B 17/3203 604/22 |
| 2011/0040404 A1 | 2/2011 | Diolaiti et al. |
| 2011/0046441 A1 | 2/2011 | Wiltshire et al. |
| 2011/0106102 A1 | 5/2011 | Balicki et al. |
| 2011/0306836 A1 | 12/2011 | Ohline et al. |
| 2012/0138586 A1 | 6/2012 | Webster et al. |
| 2012/0172786 A1 * | 7/2012 | MacKool ............. A61M 1/0084 604/22 |
| 2012/0283747 A1 | 11/2012 | Popovic |
| 2013/0116714 A1 * | 5/2013 | Adams ............. A61B 17/22012 606/159 |
| 2013/0144116 A1 | 6/2013 | Cooper et al. |
| 2014/0142591 A1 | 5/2014 | Alvarez et al. |
| 2014/0276594 A1 | 9/2014 | Tanner et al. |
| 2014/0309649 A1 | 10/2014 | Alvarez et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |

FOREIGN PATENT DOCUMENTS

| | | |
|---|---|---|
| WO | WO 03/096871 A2 | 11/2003 |
| WO | WO 2004/105849 A1 | 12/2004 |
| WO | WO 2011/161218 A1 | 12/2011 |

OTHER PUBLICATIONS

European search report and search opinion dated Jul. 2, 2015 for EP Application No. 12856685.8.
Office action dated Jun. 11, 2015 for U.S. Appl. No. 14/158,548.
U.S. Appl. No. 14/196,953, filed Mar. 4, 2014, Alvarez et al.
U.S. Appl. No. 14/201,610, filed Mar. 7, 2014, Romo.
U.S. Appl. No. 14/301,871, filed Jun. 11, 2014, Alvarez et al.
U.S. Appl. No. 14/458,042, filed Aug. 12, 2014, Kintz.
U.S. Appl. No. 14/479,095, filed Sep. 5, 2014, Romo et al.
U.S. Appl. No. 14/523,760, filed Oct. 24, 2014, Alvarez et al.
U.S. Appl. No. 14/542,373, filed Nov. 14, 2014, Romo et al.
U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345.Published Oct. 20, 2011.
Verdaasdonk, et al. Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.

* cited by examiner

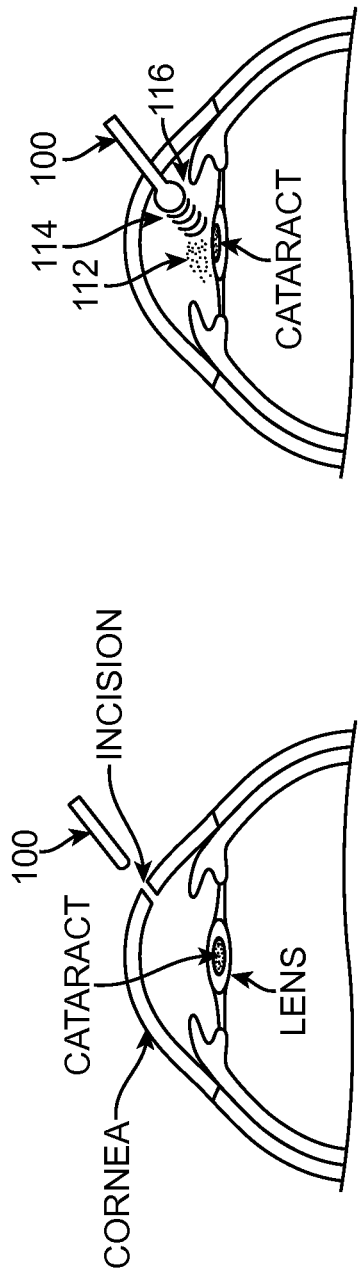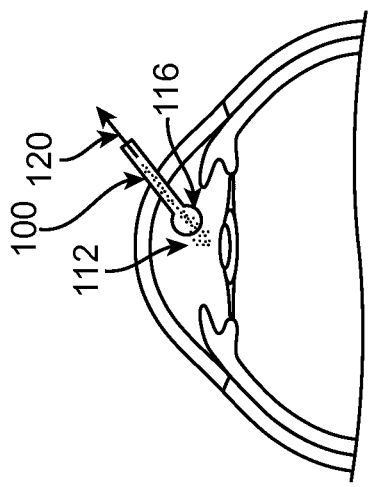

LITHOTRIPSY EYE TREATMENT

CROSS-REFERENCE OF RELATED APPLICATION

This application claims priority to U.S. Provisional Application No. 61/576,629 filed Dec. 16, 2011, the entire contents of which are hereby incorporated by reference.

BACKGROUND OF THE INVENTION

1. Field of the Invention

The field of the present application pertains to medical devices. More particularly, the field of the invention pertains to a method for using lithotripsy to treat eye conditions or paranasal sinus conditions.

2. Description of the Background Art

A cataract is a clouding of the lens in the eye that affects vision. Most cataracts are related to aging. Cataracts are very common in older people. By age 80, more than half of all Americans either have a cataract or have had cataract surgery.

The lens lies behind the iris and the pupil. It works much like a camera lens. It focuses light onto the retina at the back of the eye, where an image is recorded. The lens also adjusts the eye's focus, letting us see things clearly both up close and far away. The lens is made of mostly water and protein. The protein is arranged in a precise way that keeps the lens clear and lets light pass through it. But as we age, some of the protein may clump together and start to cloud a small area of the lens. This is a cataract. Over time, the cataract may grow larger and cloud more of the lens, making it harder to see.

Age-related cataracts can affect vision in two ways. First, clumps of protein reduce the sharpness of the image reaching the retina. The lens consists mostly of water and protein. When the protein clumps up, it clouds the lens and reduces the light that reaches the retina. The clouding may become severe enough to cause blurred vision. Most age-related cataracts develop from protein clumping. Second, the clear lens slowly changes to a yellowish/brownish color, adding a brownish tint to vision. As the clear lens slowly colors with age, it may gradually cause vision to have a brownish shade. At first, the amount of tinting may be small and may not cause a vision problem. Over time, increased tinting may make it more difficult to read and perform other routine activities.

Surgery is the only real treatment for cataracts. Each year, cataract surgeons in the United States perform over three million cataract surgeries. One of the more conventional cataract surgery procedures is called extracapsular cataract extraction (ECCE). Extracapsular cataract extraction involves the removal of almost the entire natural lens while the elastic lens capsule (posterior capsule) is left intact to allow implantation of an intraocular lens. It involves manual expression of the lens through a large (usually 10-12 mm) incision made in the cornea or sclera. Although it requires a larger incision and the use of stitches, the conventional method may be indicated for patients with very hard cataracts or other situations in which phacoemulsification is problematic.

Modern cataract surgery is usually performed using a microsurgical technique called phacoemulsfication, whereby the cataract is emulsified with an ultrasonic handpiece and then suctioned out of the eye. Before phacoemulsification can be performed, one or more incisions are made in the eye to allow the introduction of surgical instruments. The surgeon then removes the anterior face of the capsule that contains the lens inside the eye. A phacoemulsification probe is an ultrasonic handpiece with a titanium or steel needle. The tip of the needle vibrates at ultrasonic frequency to sculpt and emulsify the cataract while a pump aspirates particles through the tip. In some techniques, a second fine steel instrument called a chopper is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only. As with other cataract extraction procedures, an intraocular lens implant (IOL), is placed into the remaining lens capsule.

One possible improvement to phacoemulsification is a cataract surgery performed with lasers. Femtosecond Laser cataract surgery is rapidly emerging as a potential technology that may allow for improved precision of incision formation and emulsification of the cataract.

Although phacoemulsification and laser-based cataract surgery work well for many patients, these technologies have several shortcomings. For example, phacoemulsification ultrasound probes must propagate ultrasound energy along the length of the probe, from a proximal transducer to a distal tip. This propagation may lead to transmission of ultrasound energy along the probe to tissues in and around the eye that do not benefit from the transmission. Ultrasound probes also tend to generate more heat than would be desirable for a procedure in the eye. Finally, it may be quite difficult to steer an ultrasound probe around corners or bends, due to the mechanical requirements of propagating the ultrasound wave along the entire instrument. In other words, the probe may have to be rigid or at least more rigid than would be desirable.

Lasers have similar drawbacks. They may generate unwanted heat in the eye and are often difficult to control, thus risking damage to important nearby tissues. They also are easily damaged when attempting to navigate tight corners, as fibers in a laser probe may easily break.

Therefore, it would be advantageous to have a method and device for treating cataracts, and potentially other eye ailments, that included many of the advantages of phacoemulsification and laser procedures without at least some of the drawbacks. Ideally, such a method and device would be relatively simple to manufacture and implement, and would work well for performing cataract surgery without harming surrounding eye tissue. Also ideally, the method and/or device would be applicable to one or more other eye conditions.

Many people worldwide are afflicted by chronic or acute intermittent sinusitis, and it can often be a debilitating disease that affects one's ability to exercise, breathe, fly on airplanes, and the like. Chronic or acute intermittent sinusitis sufferers often experience symptoms such as drainage of a thick, yellow or greenish discharge from the nose or down the back of the throat, nasal obstruction or congestion, causing difficulty breathing through your nose, pain, tenderness and swelling around the eyes, cheeks, nose or forehead, reduced sense of smell and taste, ear pain, aching in the upper jaw and teeth, cough, which may be worse at night, sore throat, bad breath (halitosis), fatigue or irritability and nausea. Several types of surgical procedures have been developed to treat chronic sinusitis, such as functional endoscopic sinus surgery ("FESS") and balloon sinuplasty. FESS is very invasive, however, and requires a long and painful recovery process. Balloon sinuplasty is less invasive but is not effective in all patients.

Therefore, it would be beneficial to have a new method and device for treating chronic and/or acute intermittent sinusitis. Ideally, such a method and device would be minimally invasive and require minimal recovery time. At least some of these objectives, as well as at least some of the objectives discussed above, will be met by the embodiments described herein.

SUMMARY OF THE INVENTION

Embodiments described herein are directed to a method and device for treating eye conditions using lithotripsy. Specifically, in one embodiment, a lithotripsy probe may be used for treating a cataract in an eye. In other embodiments, a lithotripsy device may be used in other parts of the body to treat other conditions. For example, in one embodiment, a lithotripsy probe may be used to treat sinusitis by enlarging a sinus opening. In all the embodiments described herein, a spark generating/lithotripsy probe may be used as part of a robotic surgery system. The robotic surgery system may include features such as probe articulation, 3D visualization, spatial orientation of the probe, and/or the like. Although the robotic systems are not described in detail herein, any suitable system may be used, including systems currently available or those invented in the future.

In one aspect of the invention, a method of treating a cataract in an eye may involve advancing a distal end of a lithotripsy probe into the eye in proximity with the cataract, activating the lithotripsy probe to break the cataract into multiple pieces, and aspirating the multiple pieces of the cataract out of the eye using suction. The terms "breaking" and "breaking into multiple pieces" also encompass emulsification, liquidation, aerosolization, and the like. Various embodiments described herein may break one or more large pieces of tissue (cataract, mucosa, bone, etc.) into multiple smaller pieces, and any such process is covered by the embodiments described herein. Furthermore, a "lithotripsy probe" may mean any probe in which a spark may be generated.

In some embodiments, accessing the eye may include making an incision in a cornea of the eye and advancing the probe through the incision. In some embodiments, activating the lithotripsy probe may involve generating a spark between two wires disposed in the probe. For example, the spark may be generated between two tips of the two wires disposed closer to the distal end of the probe than to a proximal end of the probe. the probe contains a fluid, wherein activating the lithotripsy probe generates a motion of the fluid, and wherein the motion of the fluid causes the cataract to break into the multiple pieces. In some embodiments, the method may further involve inflating a balloon on the probe.

Typically, but not necessarily, the multiple pieces may be aspirated via an aspiration lumen of the probe. Also, the method may further include irrigating the eye using irrigation fluid dispensed out of an irrigation lumen of the probe. Some embodiments may include aspiration and irrigation via separate lumens, while alternative embodiments may use a common lumen. Optionally, the method may further involve steering the lithotripsy probe around a corner before the activating step.

In another aspect of the present invention, a method of removing an unwanted structure from an eye may involve advancing a distal end of a probe into the eye in proximity with the unwanted structure in the eye, generating a spark within the probe to produce a forward moving force in a fluid in the probe, where the forwardly moving fluid breaks the unwanted structure into multiple pieces, and aspirating the multiple pieces of the unwanted structure out of the eye using suction. In one embodiment, the unwanted structure comprises a cataract.

In another aspect of the present invention, a method of treating a cataract in an eye may involve activating a spark generating device to break the cataract into multiple pieces and aspirating the multiple pieces of the cataract out of the eye.

In yet another aspect of the present invention, a device for performing cataract surgery may include: an elongate probe having a proximal end, a distal end, and at least one lumen extending longitudinally through at least a portion of the probe between the proximal and distal ends; two spark-transmitting wires or electrodes disposed in the at least one lumen, where tips of the two wires or electrodes are disposed near one another and closer to the distal end than to the proximal end of the probe; and a spark generator at or near the proximal end of the probe and coupled with the two wires or electrodes to generate a spark across the tips.

In some embodiments, the lumen includes a first lumen in which the wires are disposed and at least a second lumen for aspiration. In some embodiments, the second lumen is a combined aspiration/irrigation lumen. Some embodiments may further include a third lumen for irrigation. In some embodiments, each of the two wires is disposed in a separate lumen. Optionally the probe may further include means for articulating the probe. For example, in one embodiment, the probe includes three, concentric, flexible, pre-formed tubes, each of which has a different shape, and each of which is connected proximally to an actuator, wherein each of the tubes is free to translate and rotate relative to the other tubes via the actuators. Optionally, the device may further include a membrane covering the distal end of the probe. The device may further include a fluid disposed in the probe.

In another aspect of the present invention, a device for performing cataract surgery may include: an elongate probe having a proximal end, a distal end, and at least one lumen extending longitudinally through at least a portion of the probe between the proximal and distal ends; a fluid disposed in the probe; and a wave generator disposed in the probe for forming waves in the fluid to break up the cataract. For example, the wave generator may be a spark generator.

In another aspect of the present invention, a method for treating sinusitis may involve advancing a probe into a sinus opening, inflating a balloon on the probe in the sinus opening, using an inflation fluid; and generating a wave in the inflation fluid to alter a shape of a bone forming the sinus opening, thus enlarging the opening. In some embodiments, generating the wave comprises generating a spark between two wires disposed in the probe.

In another aspect of the present invention, a method for treating sinusitis may involve using lithotripsy to enlarge a sinus opening. For example, in one embodiment, the lithotripsy probe may be inserted into a nostril and advanced to a location near a sinus opening, and the probe may then be activated to enlarge the opening. Particles or debris may be aspirated in some embodiments through the probe.

These and other aspects and embodiments will be described in greater detail below, in reference to the attached drawing figures.

BRIEF DESCRIPTION OF THE DRAWINGS

FIGS. 3A-3C are side, cross-sectional views of a portion of an eye, illustrating a method for using a lithotripsy probe to perform cataract surgery, according to one embodiment of the present invention;

DETAILED DESCRIPTION OF THE PREFERRED EMBODIMENT

Figure 1:
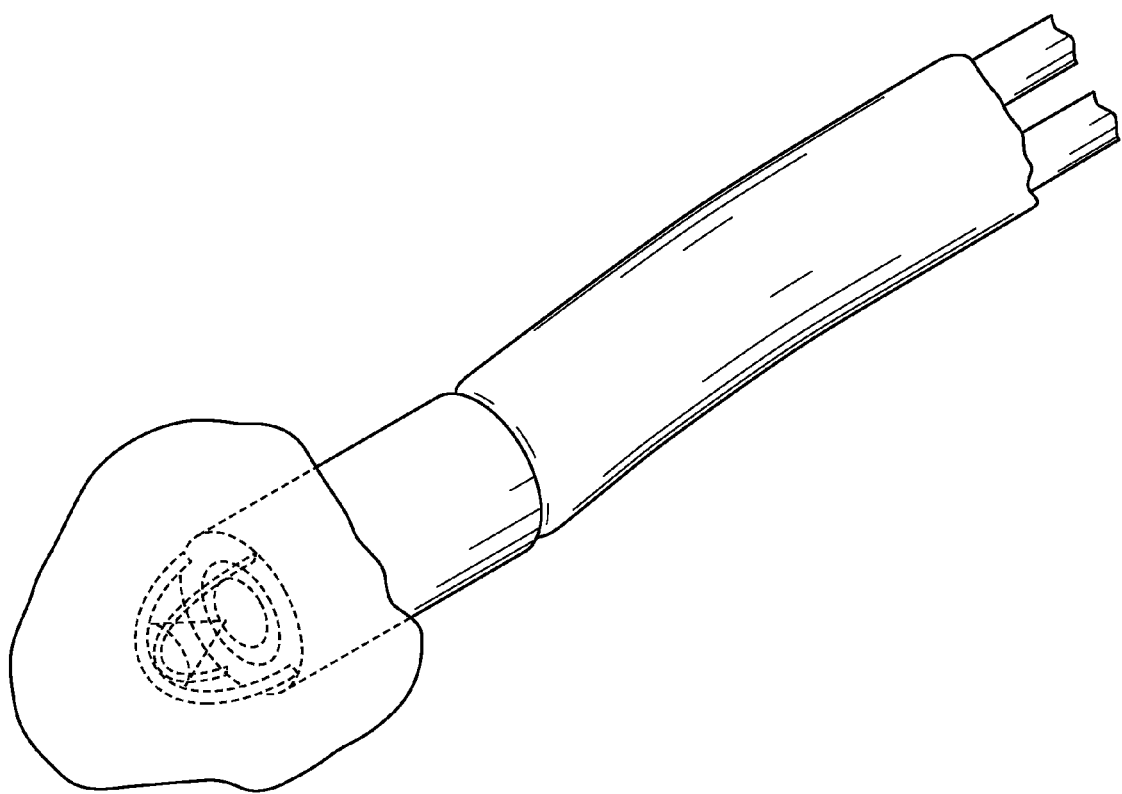
FIG. 1 is a perspective view of a distal portion of a lithotripsy probe, according to one embodiment of the present invention.

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to a method and device for treating eye conditions or sinus conditions using a spark generating (or "lithotripsy") probe. (The terms "spark generating probe" and "lithotripsy probe" are used interchangeably herein and should not be interpreted to limit one another in any way.) A spark generating probe may be used to generate a shock wave, which may be used to disrupt, break apart and in some cases emulsify tissue. In the case of a cataract in an eye, a spark generating probe may be used to break apart a cataract into multiple, smaller pieces, which may then be suctioned from the eye using the probe or other suction means. Although the method and device are typically described below in the context of treating cataracts, in various alternative embodiments, other eye conditions may be treated. As mentioned farther below, the present disclosure is also directed to a method and device for enlarging an opening into a paranasal sinus cavity to treat sinusitis.

It may be advantageous to incorporate any of the lithotripsy probes described herein into a robotic surgery/delivery system. For example, any of the spark generating probes may be incorporated into the da Vinci® Surgical System, provided by Intuitive Surgical, Inc., (www.intuitivesurgical.com) or the Magellan™ Robotic System, provided by Hansen Medical, Inc. (www.hansenmedical.com). Robotic surgical systems such as (but not limited to) these examples may help provide precise movement and 3D imaging of a spark generating probe and/or a surgical target site that may help ensure the probe is delivered and held in a position such that, when fired, the shock wave from the probe is transmitted to target tissue and spares injury to surrounding tissue. A number of robotic surgery systems are presently known, and others may be developed specifically for use with the lithotripsy probes and methods described herein. Although the robotic systems are not described in detail in this application, any suitable systems may be used with or incorporated with the probe embodiments described.

In one embodiment, a lithotripsy probe for treating cataracts (or other conditions) may be an electrohydraulic lithotripsy ("EHL") probe that creates a substantially annular shockwave. Such EHL probes are described, for example, in U.S. Patent Application Pub. No. 2010/0036294 (application Ser. No. 12/436,547, filed by Mantell et al.), the full disclosure of which is hereby incorporated by reference. The present application also fully incorporates by reference U.S. Pat. No. 4,597,388, issued to Koziol et al. EHL probes include a first electrode at a distal end of the probe, and a second electrode coaxially aligned with the first electrode. A difference in voltage polarities between the first and second electrodes causes an electric arc, resulting in a shockwave that is at least semi-annular that radiates from the lithotripsy probe.

Figure 2:
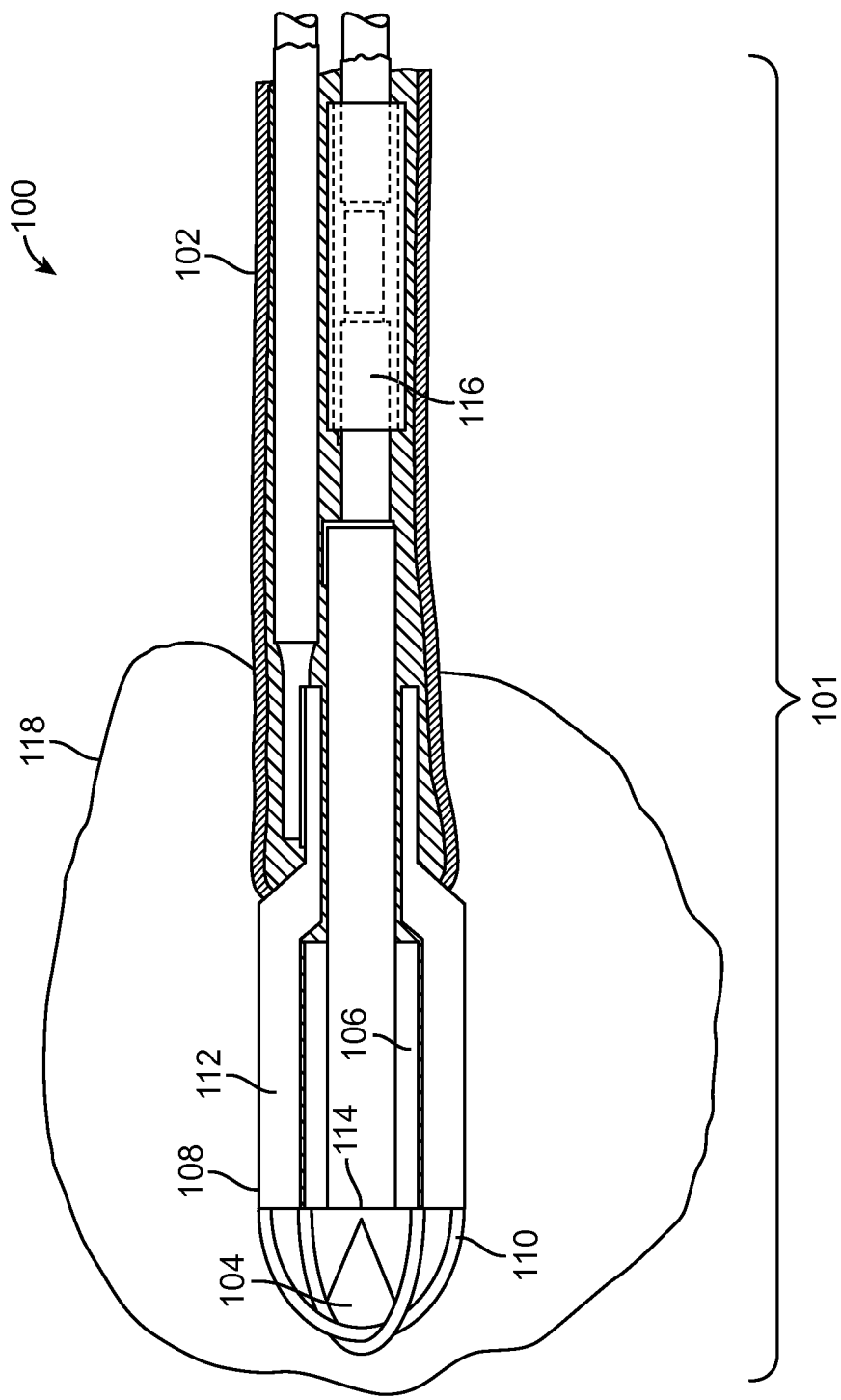
FIG. 2 is a side, cross-sectional view a portion of the lithotripsy probe of FIG. 1.

Referring to FIGS. 1 and 2, one embodiment of a radially-firing EHL probe 100 (the "probe 100") includes a lithotripsy probe tip 101 including an insulating body 102, a first electrode 104, and a second electrode 106. In one embodiment, the first electrode 104 is positioned at a first distal end 108 of the lithotripsy probe tip 101. In one implementation, the first electrode 104 is conic in shape and includes an electrically conductive material such as copper, silver, or stainless steels. However, the first electrode 104 may be other shapes such as a curved surface and/or made of other electrically conductive material. In alternative embodiments, the electrodes 104, 106 may be aligned side by side and may even be distal tips of wires disposed within probe 100.

The first electrode 104 is supported by a plurality of wires 110 extending from a distal end 108 of the lithotripsy probe tip 101. The wires 110 may be made of an electrically conductive material, such as copper, silver, stainless steel, or other conductive materials, and electrically coupled with a first electrically conductive structure 112 in the EHL probe 100. Typically, the wires 110 are insulated other than where they are electrically coupled with the first electrode 104 and the first electrically conductive structure 112. As known in the art, the first conductive structure 112 may be coupled with an electrical source, such as an electrohydraulic generator (Autolith, Supplied by Northgate Technologies, Inc.), used to charge the first electrode 104 to a first polarity.

The second electrode 106 is positioned in the body of the lithotripsy probe tip 101. In one implementation, at least an end 114 of the second electrode 106 is cylindrical and includes an electrically conductive material such as copper, silver, stainless steel, or other conductive materials. However, the second electrode 106 may be other shapes. The second electrode 106 is positioned in the lithotripsy probe tip 101 such that the second electrode 106 is coaxially, and in some embodiments symmetrically, aligned with the first electrode 104. For example, when the first electrode 104 is conic in shape and an end 114 of the second electrode 106 is cylindrical, the first and second electrodes 104, 106 are positioned such that an axis extending from the conic first electrode 104 is substantially aligned with an axis extending from the cylindrical portion of the second electrode 106.

In one embodiment, the first electrode 104 may be an anode and the second electrode 106 may be a cathode, where in other embodiments, the first electrode 104 may be a cathode and the second electrode 106 may be an anode. When the first electrode 104 is charged to a first polarity via the first conductive structure 112 and the second electrode 106 is charged to a second, opposite polarity via the second conductive structure 114, a discharge of electricity occurs between the first and second electrodes 104, 106 (an electrical arc) when the potential between the first and second electrodes 104, 106 reaches the breakdown voltage for the media separating the electrodes.

In some embodiments, at least a portion of the lithotripsy probe tip 101 including the first and second electrodes 104, 106 may be surrounded by a flexible encapsulating member 118, such as a balloon, comprising a water-tight flexible material, such as Mylar. The flexible encapsulating member 118 encapsulates a liquid such as saline or other suitable liquid. When an electrical arc occurs between the first and second electrodes 104, 106 as described above, the electrical arc causes a steam bubble in the liquid of the flexible encapsulating member 118. The steam bubble rapidly expands and contracts back on itself. As the steam bubble contracts, a pressure wave (a shockwave) is created in the liquid of the flexible encapsulating member 118 that radiates away from the lithotripsy tip 101 in a substantially radial manner such that the shockwave is at least semi-annular. However, in other embodiments, a flexible encapsulating member 118 may not surround the lithotripsy probe tip 101.

In some embodiments, it may be possible to fill flexible encapsulating member 118 with a colored fluid, such as India ink. A colored fluid may absorb some or all of the ultraviolet light generated when the probe 100 sparks. This may be advantageous especially for use in the eye, where unwanted ultraviolet light exposure may cause damage to surrounding eye tissue.

Various embodiments of the lithotripsy probe 100 may contain any of a number of different lumens. For example, the probe 100 may include one lumen containing fluid and electrodes and one lumen for suction. Alternatively or additionally, the probe 100 may contain a separate irrigation lumen. Each lumen, in turn, may have a corresponding port at or near the proximal end of the device.

Other embodiments and features of various EHL probes are described further in U.S. Patent Application Pub. No. 2010/0036294, which was previously incorporated by reference.

Turning now to FIGS. 3A-3C, one embodiment of a method for treating a cataract is illustrated. For convenience, only a distal portion of the probe 100 is illustrated in these figures. Proximally, the probe 100 will be attached to a spark generator. Also, in various alternative embodiments of the method, the probe 100 may either handheld or coupled with a robotic surgery system. Thus, the present description may be applied to any delivery method of the probe 100, whether robotic or not. Any suitable imaging system may be incorporated as well, sometimes as part of the robotic system. Three dimensional imaging is but one example.

In FIG. 3A, a portion of an eye is shown in cross-section, including a cornea, lens and cataract, with an incision formed in the cornea. The lithotripsy probe 100 (as described above or some alternative embodiment) may be inserted through the incision, as shown in FIG. 3B. Also as shown in FIG. 3B, once in a desired position relative to the lens, an inflatable balloon tip 116 may be inflated. As previously mentioned, in some embodiments the balloon tip 116 may be inflated with light absorbing inflation fluid, such as any suitable dye, dyed saline solution, India ink, diluted India ink or the like. The spark generator (not pictured) may them be used to generated a spark in the probe 100, which will propagate a shock wave 114, which may be used to break up the cataract into small pieces 112 (or emulsify the cataract). Once the cataract is fully broken up or emulsified, as shown in FIG. 3C, the pieces of cataract may be sucked up into the probe 100 via suction 120 applied at or near a proximal end (not shown) of the probe 100. Alternatively, a separate suction device may be used. Once the cataract is removed, an intraocular lens (IOL) implant may be implanted, typically through the same incision.

Figure 4:
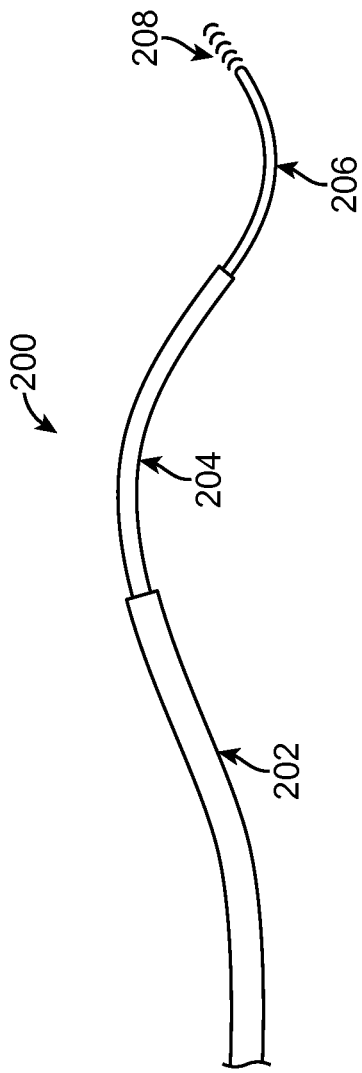
FIG. 4 is a perspective view of a distal portion of a lithotripsy probe, according to another embodiment of the present invention.

Referring now to FIG. 4, in another embodiment, a lithotripsy probe 200 may include means for articulating. In this embodiment, the probe 200 includes a proximal portion 202 having a first shape, and middle portion 204 having a second shape, and a distal portion 206 having a third shape. Housed within probe 200 is a spark generator (not visible) that generates a fluidic wave 208 for performing procedures as described above. The three portions 202, 204, 206 are at least slightly flexible and are free to rotate and translate relative to one another. Furthermore, they all have a predetermined shape and are configured to resume their predetermined shape when not constrained. By translating and/or rotating the different portions 202, 204, 206, it is possible to steer the probe 200 in many different directions. Examples of such probes are described in further detail, for example, in U.S. Patent Application Pub. No. 2009/0171271 (application Ser. No. 12/084,979, filed by Webster et al.) and U.S. Pat. No. 7,883,475, issued to Dupont et al., the full disclosures of which are hereby incorporated by reference.

In alternative embodiments, any other suitable type of articulation mechanism may be used to articulate a probe. Examples include, but are not limited to, cam mechanisms, pull wires, slotted tubes and the like.

Figure 5A:
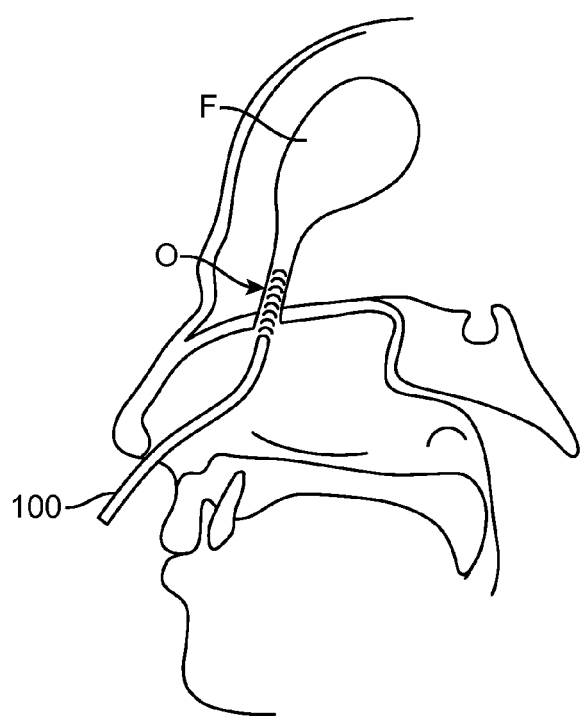
FIGS. 5A and 5B are cross-sectional side views of a human head, illustrating a method for treating sinusitis using a lithotripsy probe, according to one embodiment of the present invention.
Figure 5B:
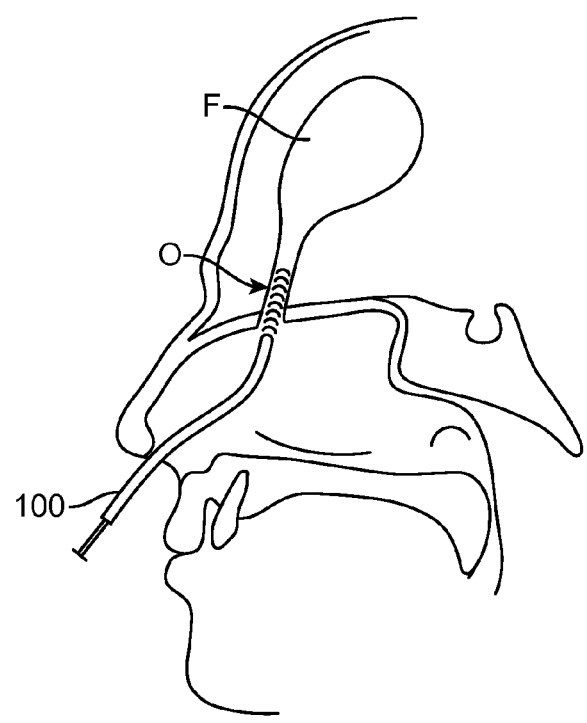

With reference now to FIGS. 5A and 5B, a method for treating a sinus is illustrated. Many people worldwide are afflicted by chronic or acute intermittent sinusitis, and it can often be a debilitating disease that affects one's ability to exercise, breathe, fly on airplanes, etc., as well as often causing crippling headaches and profuse nasal discharge. Several types of surgical procedures have been developed to treat chronic sinusitis, such as functional endoscopic sinus surgery ("FESS") and balloon sinuplasty. FESS is very invasive, however, and requires a long and painful recovery process. Balloon sinuplasty is less invasive but is not effective in all patients. It may be possible to use the lithotripsy probe 100 described herein (or other embodiments of lithotripsy probes) to enlarge a sinus opening and thus ameliorate sinusitis.

In FIG. 5A, a human head is shown in cross section, including a frontal sinus F and an opening O to the frontal sinus F. The distal end of the probe 100 is positioned near the beginning of the opening O of the sinus and is generating a fluidic wave directed at the opening. As shown in FIG. 5B, lithotripsy may act to enlarge the sinus opening, thus ameliorating sinusitis. It may enlarge the opening by effecting mucosal tissue, bone, or both. In some cases, sinus opening tissue may be broken into smaller pieces or emulsified, and debris may be suctioned via the probe 100. In some embodiments, an inflatable balloon tip may be incorporated into the probe 100, as described above. This method may be performed on frontal, maxillary, sphenoid and even ethmoid sinuses.

Figure 6A:
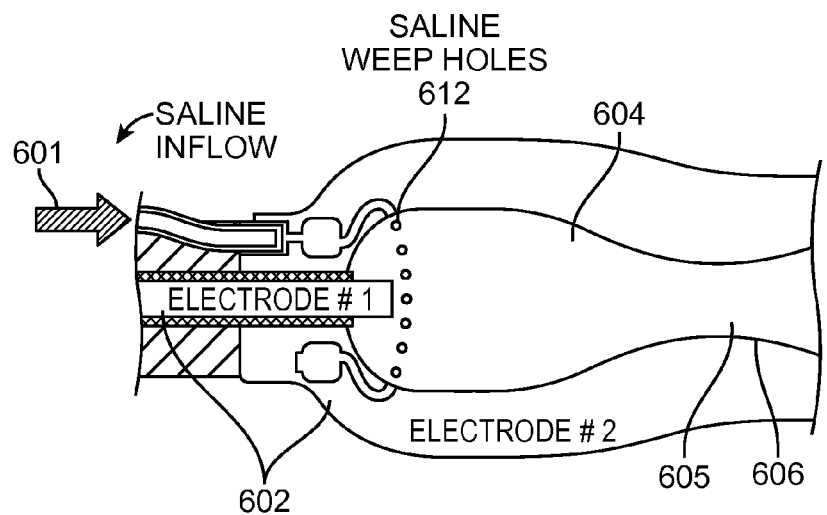
FIGS. 6A and 6B are cross-sectional side views of one embodiment of a nozzle, according to one embodiment that may be attached to an end of the probe depicted in FIG. 2.

FIGS. 6A and 6E are cross-sectional side views of a nozzle, according to one embodiment that may be attached to an end of the probe depicted in FIG. 2.

In FIG. 6A, an electrode pair 602 is depicted. Also, a tube 601 facilitates an inflow for saline to transport saline to a plurality of saline weep hole 612. In this embodiment, a nozzle (depicted as the hourglass figure of three portions 604, 605, and 606) may be used in conjunction with FIG. 2. The first portion of the nozzle is a convergent section (depicted as 604), while the second portion is a throat section (605), and a final portion is a divergent section 606. This type of nozzle facilitates a controlled sonic wave that is output at a higher speed from the section 606 as compared to the first section 604.

As previously described in previous figures, the spark generator (not pictured) may them be used to generated a spark in the probe 100, which will propagate a shock wave 114, Which may be used to break up the cataract into small pieces 112 (or emulsify the cataract). Once the cataract is fully broken up or emulsified, as shown in FIG. 3C, the pieces of cataract may be sucked up into the probe 100 via suction 120 applied at or near a proximal end (not shown) of the probe 100.

Figure 6B:
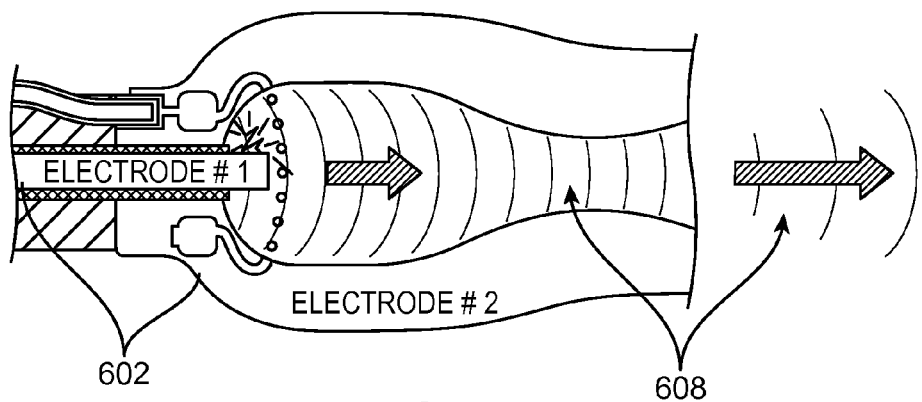

In FIG. 6B, the resulting shock wave 608 that is output at a higher speed from section 606 as compared to the first section 608.

Figure 6C:
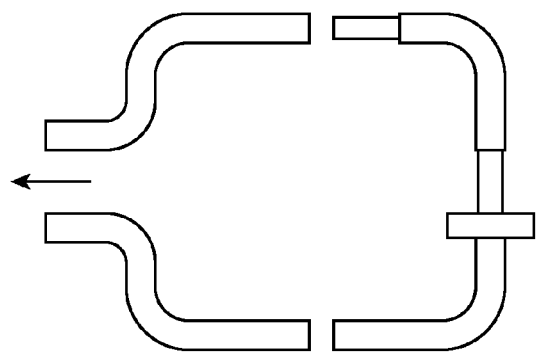
FIG. 6C is a cross-sectional side view of another embodiment of a nozzle, according to one embodiment that may be attached to an end of the probe depicted in FIG. 2.

In FIG. 6C, a different nozzle configuration is depicted. In this embodiment, the resulting shock wave that is output is directionally controlled by the opening depicted by the arrow.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

The invention claimed is:

1. A method of treating a cataract in an eye, the method comprising:
   advancing a distal end of a lithotripsy probe into the eye in proximity with the cataract;
   activating the lithotripsy probe to break the cataract into multiple pieces by causing fluid to move forward from a nozzle at the distal end of the lithotripsy probe, wherein causing fluid to move forward from the nozzle comprises generating a shock wave in the nozzle near the distal end of the lithotripsy probe, and wherein an hourglass shape of the nozzle increases a speed of the shock wave at an output opening of the nozzle; and
   aspirating the multiple pieces of the cataract out of the eye using suction.

2. The method of claim 1, wherein generating the shock wave comprises generating a spark between two wires disposed in the probe.

3. The method of claim 2, wherein the spark is generated between two tips of the two wires disposed closer to the distal end of the probe than to a proximal end of the probe.

4. The method of claim 1, further comprising inflating a balloon on the probe.

5. The method of claim 1, wherein the multiple pieces are aspirated via an aspiration lumen of the probe.

6. The method of claim 1, further including irrigating the eye using irrigation fluid dispensed out of an irrigation lumen of the probe.

7. The method of claim 1, further comprising steering the lithotripsy probe around a corner before the activating step.

8. The method of claim 1, wherein the steps are performed via a robotic surgical system to which the probe is attached.

9. The method of claim 1, wherein the hourglass-shaped nozzle has a convergent proximal section, a middle throat section, and a divergent distal portion ending at the output opening.

10. The method of claim 9, wherein the hourglass-shape causes the forwardly moving shock wave at the divergent distal portion to leave the output opening at a higher speed than at the convergent proximal section.

11. A method of removing an unwanted structure from an eye, the method comprising:
    advancing a distal end of a probe into the eye in proximity with the unwanted structure in the eye;
    generating a spark within the probe to produce a forward moving shock wave force in a fluid in the probe, wherein the forwardly moving shock wave breaks the unwanted structure into multiple pieces, and wherein the forwardly moving shock wave is directed from a nozzle at the end of the probe, the nozzle having an hourglass shape to increase a speed of the shock wave at an output opening of the nozzle; and
    aspirating the multiple pieces of the unwanted structure out of the eye using suction.

12. The method of claim 11, wherein the unwanted structure comprises a cataract.

13. The method of claim 11, wherein the hourglass-shaped nozzle has a convergent proximal section, a middle throat section, and a divergent distal portion ending at the output opening.

14. The method of claim 13, wherein the hourglass-shape causes the forwardly moving shock wave at the divergent distal portion to leave the output opening at a higher speed than at the convergent proximal section.

* * * * *